United States Patent [19]

Yoshida et al.

[11] Patent Number: 5,311,852

[45] Date of Patent: May 17, 1994

[54] METHOD FOR DETECTING FUEL BLENDING RATIO

[75] Inventors: Masato Yoshida, Kyoto; Takanao Yokoyama, Nagaokakyo; Muneyoshi Nanba, Kyoto; Yoshihiko Kato, Kyoto; Kazumasa Iida, Kyoto; Katsuhiko Miyamoto, Kyoto, all of Japan

[73] Assignee: Mitsubishi Jidosha Kogyo Kabushiki Kaisha, Tokyo, Japan

[21] Appl. No.: 113,685

[22] Filed: Aug. 31, 1993

Related U.S. Application Data

[62] Division Ser. No. 752,452, filed as PCT/JP91/00032, Jan. 16, 1991, Pat. No. 5,263,464.

[30] Foreign Application Priority Data

Jan. 19, 1990 [JP] Japan .................................. 2-11515

[51] Int. Cl.$^5$ .............................................. F02D 41/14
[52] U.S. Cl. .................................... 123/674; 123/494
[58] Field of Search ............... 123/1 A, 478, 480, 494, 123/674, 675, 689, 690, 694, 696

[56] References Cited

U.S. PATENT DOCUMENTS

| | | | |
|---|---|---|---|
| 4,706,629 | 11/1987 | Wineland et al. | 123/494 |
| 4,909,225 | 3/1990 | Gonze et al. | 123/494 |
| 4,945,880 | 8/1990 | Gonze et al. | 123/674 |
| 4,986,241 | 1/1991 | Inoue et al. | 123/690 X |
| 5,163,407 | 11/1992 | Yoshida et al. | 123/674 X |
| 5,170,763 | 12/1992 | Kitajima et al. | 123/494 X |
| 5,178,121 | 1/1993 | Kitajima et al. | 123/689 |
| 5,195,497 | 3/1993 | Yoshida et al. | 123/696 |
| 5,197,450 | 3/1993 | Kitajima et al. | 123/690 X |
| 5,197,451 | 3/1993 | Yoshida et al. | 123/696 |

FOREIGN PATENT DOCUMENTS

| | | |
|---|---|---|
| 5131 | 1/1988 | Japan . |
| 244133 | 9/1989 | Japan . |
| 256848 | 10/1989 | Japan . |

Primary Examiner—Willis R. Wolfe

[57] ABSTRACT

In a fuel blending ratio detecting method, a first blending ratio of the methanol in the fuel supplied to an internal combustion engine is detected by a blending ratio sensor; an air/fuel ratio feedback compensation coefficient computed on the basis of an output of an $O_2$ sensor is used to compute a feedback learned value, and the current blending ratio compensation coefficient is multiplied by this value to compute the next blending ratio compensation coefficient so as to obtain a second blending ratio; the current blending ratio compensation coefficient is multiplied by a peak mean value of the computed feedback compensation coefficient to compute the next blending ratio compensation coefficient so as to obtain a third blending ratio; and the first, second or third blending ratio is selected according to the operating conditions of the internal combustion engine. Thus, the selected blending ratio is always used as the control blending ratio very close to the true ratio, so that the internal combustion engine can be accurately controlled.

6 Claims, 11 Drawing Sheets

METHOD FOR DETECTING FUEL BLENDING RATIO

This application is a divisional of copending application Ser. No. 07/752,452, filed as PCT/TP91/00032, Jan. 16, 1991, now U.S. Pat. No. 5,263,464.

TECHNICAL FIELD

This invention relates to a fuel blending ratio detecting method for detecting the blending ratio of a mixed fuel supplied to an internal combustion engine.

BACKGROUND ART

Methanol is now noted as fuel giving rise to less environmental pollution, and methanol engines are also being developed now. However, immediate change-over of fuel used in all kinds of automotive vehicles from gasoline to methanol is almost impossible, and, at the time of change-over, a situation will occur where at least temporarily both the methanol fuel and the gasoline fuel are used.

With a view to deal with such a situation, introduction of a vehicle is proposed in which both the gasoline fuel and the methanol fuel can be used, that is, a vehicle which has the degree of freedom with respect to fuel to be used. (Such a vehicle will be referred to hereinafter simply as an FFV.)

In order that the engine of such a FFV can be accurately controlled, the blending ratio which is the mixing ratio of fuel between the gasoline and the methanol is to be continuously detected so as to execute various required controls on the engine. A blending ratio detective device or sensor for use in such a purpose has been developed and is now in use and can be directly associated with the fuel supply system of the engine so as to directly detect the blending ratio of the fuel.

There is also a method for detecting the blending ratio by the use of an $O_2$ sensor which generates the information of oxygen concentration in the exhaust gases of an engine, that is, the air/fuel ratio.

However, the practical use of the blending ratio sensor using a conventional photoelectric transducer is delayed due to the difficulty of temperature compensation that is frequently required due to frequent error and durability problems attributable to dirt progressively accumulating on the optical system.

On the other hand, in the case of the method using the $O_2$ sensor, the blending ratio is computed by learning on the basis of the feedback from the $O_2$ sensor. However, the blending ratio may not be detected as desired since this feedback learning control is not successfully attained until the driving conditions of the vehicle are more or less stabilized.

SUMMARY OF THE INVENTION

It is an object of the present invention to provide a fuel blending ratio detecting method capable of accurately detecting the blending ratio according to the operating conditions of an engine.

To attain the above object, the present invention provides a fuel blending ratio detecting method for an internal combustion engine having a blending ratio sensor disposed in a fuel feed path feeding fuel to the internal combustion engine so as to detect a first blending ratio of methanol, an $O_2$ sensor generating information of an air/fuel ratio in exhaust gases from the internal combustion engine, the sensor output being increased or decreased with time relative to a rich/lean decision voltage, and fuel control means computing an air/fuel ratio feedback compensation coefficient by a method including at least an integral control of the output of said $O_2$ sensor thereby regulating the quantity of supplied fuel so that an air/fuel ratio of the fuel mixture supplied to the internal combustion engine corresponds to a predetermined target value, comprising the steps of:

computing at intervals of a first predetermined period, a feedback learned value obtained as a result of said integral control on the basis of the factor of the feedback compensation coefficient, and multiplying the current blending ratio compensation coefficient by said feedback learned value to compute the next blending ratio compensation coefficient so as to compute a second blending ratio on the basis of said next blending ratio compensation coefficient;

computing a peak mean value of the current and preceding peak values of the feedback compensation coefficient each time peak values appear, and multiplying the current blending ratio compensation coefficient by said peak mean value to compute the next blending ratio compensation coefficient so as to compute a third blending ratio on the basis of said next blending ratio compensation coefficient; and selecting one of said first, second and third blending ratios according to the operating conditions of the internal combustion engine.

According to this method, one of the first blending ratio from the blending ratio sensor and the second and third blending ratios based on the air/fuel ratio information can be selectively generated as a control blending ratio.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

PREFERRED EMBODIMENTS OF THE PRESENT INVENTION

A fuel blending ratio detecting method according to an embodiment of the present invention will now be described.

Figure 1:
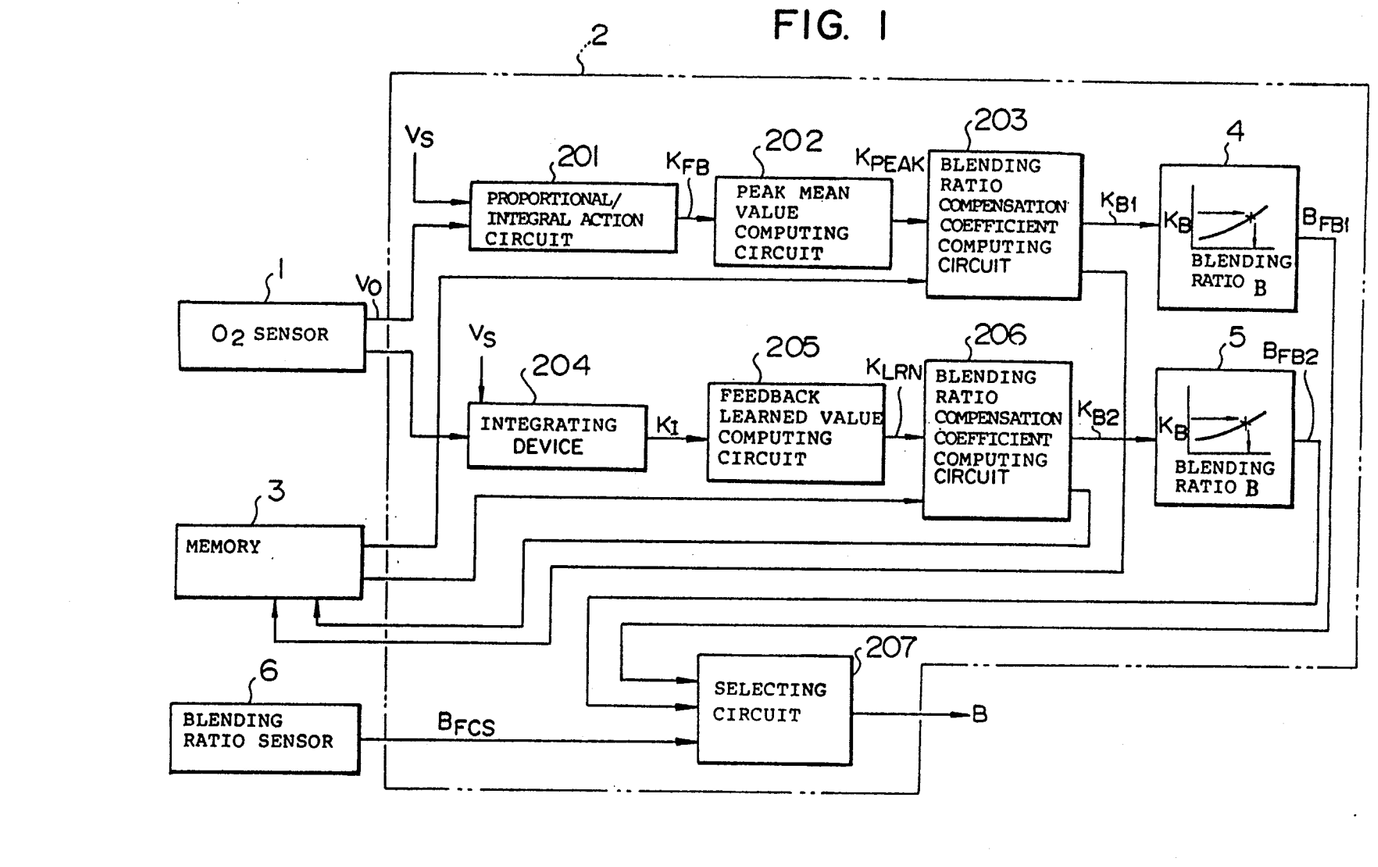
FIG. 1 is a block diagram illustrating the method for an embodiment of the present invention.

As shown in FIG. 1, this method uses a blending ratio sensor 6 generating an output indicating the blending ratio $B_{FCS}$ of gasoline and methanol in the fuel supplied to an internal combustion engine, an $O_2$ sensor 1 capable of generating air/fuel ratio information, that is, oxygen concentration information in exhaust gases of the internal combustion engine, a control device 2 for computing at least one of a first and a second feedback blending ratio $B_{FB1}$ and $B_{FB2}$ on the basis of the output $V_0$ of the sensor and selecting these values and the blending ratio $B_{FCS}$ according to a predetermined order of selection so as to generate a blending ratio B used for the control, a memory 3 for storing a first and a second blending ratio compensation coefficient $K_{B1}$ and $K_{B2}$ computed according to the blending ratio of the fuel actually supplied, and a first and a second blending ratio map 4 and 5 used for mapping the first and second blending ratio compensation coefficients $K_{B1}$ and $K_{B2}$ corresponding to respective blending ratios B.

Figure 2A:
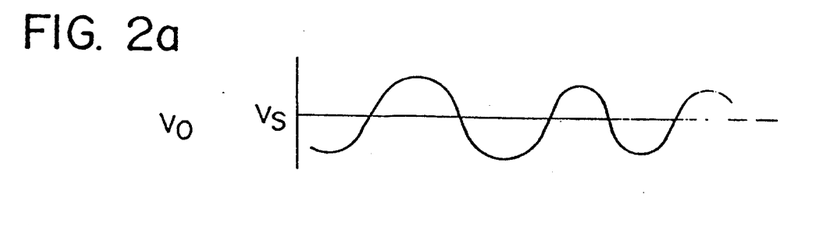
FIGS. 2a to 2f are waveform diagrams showing how an air/fuel ratio output and other characteristic values change with time according to the method for an embodiment of the present invention.

The $O_2$ sensor 1 referred to herein generates the output $V_0$ responsive to the air/fuel ratio and increased or decreased with time relative to a rich/lean decision voltage $V_S$ (the value where the concentration of oxygen in exhaust gases is regarded to be stoichiometric). (Refer to FIG. 2a.)

In the method of the present embodiment, the control device 2 first computes at least one of the first and second feedback blending ratios $B_{FB1}$ and $B_{FB2}$ on the basis of the sensor output $V_0$ of the $O_2$ sensor 1.

Figure 2B:
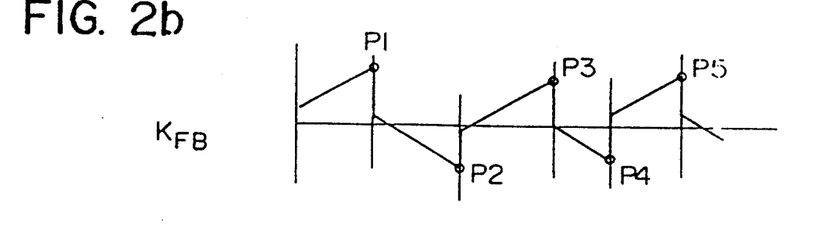

That is, the applied sensor output $V_0$ is compared with the decision voltage $V_S$ in a proportional/integral action circuit 201 in the control device 2, and depending on the magnitude of the applied sensor output $V_0$ to the decision voltage $V_S$, its proportional gain and its integral gain are proportionated and integrated to compute a feedback compensation coefficient $K_{FB}$. The compensation coefficient thus obtained shows its peak value each time the sensor output $V_0$ crosses the decision voltage $V_S$. (Refer to FIG. 2b.)

A pair of adjacent large and small values ($P_1$, $P_2$, $P_3$, ...) of the computed feedback compensation coefficient $K_{FB}$ are then successively supplied to a peak mean value computing circuit 202.

Figure 2C:
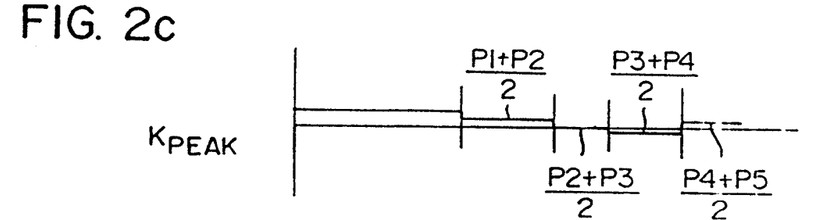

Whenever one pair of large and small peak values are newly supplied to the peak mean value computing circuit 202, the mean value $(P_{n-1}+P_n)/2$ at that time is computed. The peak main values $K_{PEAK}$ are successively obtained. (Refer to FIG. 2c.)

Then, a blending ratio compensation coefficient computing circuit 203 reads out the preceding first blending ratio compensation coefficient $K_{B1}$ from the memory 3 and multiplies that value by the peak mean value $K_{PEAK}$ to newly compute the first blending ratio compensation coefficient $K_{B1}$ which is used to update the corresponding value stored already in the memory 3.

Then, on the basis of the first blending ratio map 4, the control device 2 converts the updated first blending ratio compensation coefficient $K_{B1}$ into the first feedback blending ratio $B_{FB1}$ by back reading the first blending ratio map 4.

Figure 2D:
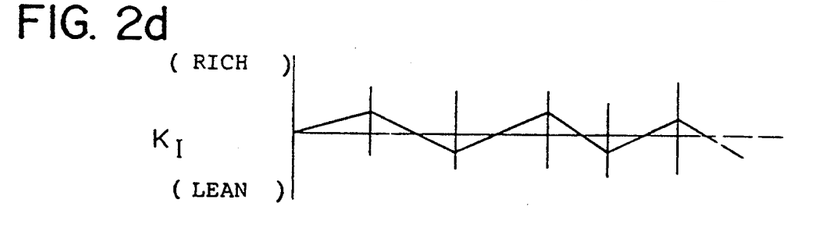

In lieu of this processing or in addition to this processing, depending on the magnitude of the air/fuel ratio responsive output $V_0$ of the $O_2$ sensor 1 relative to the decision voltage $V_S$, The integral gain is integrated by an integration device 204 in the control device 2 to provide an integral compensating term $K_1$ which is a factor of the compensation coefficient $K_{FB}$. (Refer to FID. 2d.)

Figure 2E:
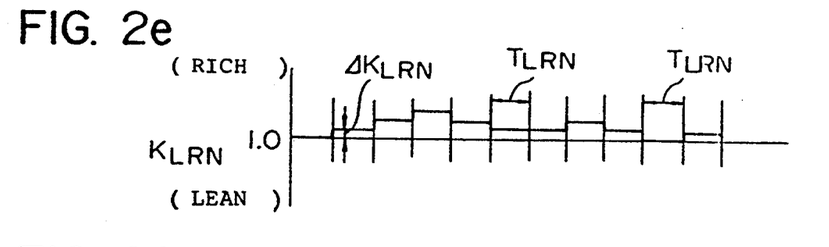
Figure 2F:
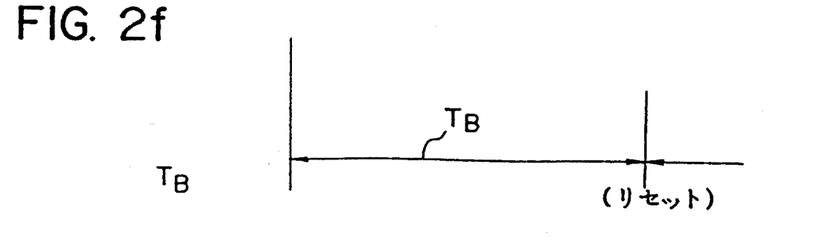

Whether the integrated value of the integral compensating term $K_1$ is positive or negative is decided in each of predetermined learning periods $T_{LRN}$ in a feedback learned value computing circuit 205, and, as a result, a feedback learned value $K_{LRN}$ is computed. That is, the feedback learned value $K_{LRN}$ referred to herein is such that, depending on whether the integral compensating term $K_1$ for the air/fuel ratio feedback compensation coefficient $K_{FB}$ described above is positive or negative, a predetermined value $\Delta K_{LRN}$ is added to or subtracted from the preceding value $K_{LRN}$. (Refer to FIG. 2e.) The feedback learned value $K_{LRN}$ updated every predetermined learning period $T_{LRN}$ is supplied to a blending ratio compensation coefficient computing circuit 206 at the end of a fixed blending ratio measuring period $T_B$. (Refer to FIG. 2f)

The blending ratio compensation coefficient computing circuit 206 reads out the preceding second blending ratio compensation coefficient $K_{B2}$ from the memory 3 and multiplies that value by the feedback learned value $K_{LRN}$ to newly compute the second blending ratio compensation coefficient $K_{B2}$ which is used to update the corresponding value stored already in the memory 3.

Then, the control device 2 back-reads the second blending ratio map 5 to convert the updated second blending ratio compensation coefficient $K_{B2}$ into the second feedback blending ratio $B_{FB2}$.

Further, the control device 2 directly reads on the basis of the output of the blending ratio sensor 6 the blending ratio $B_{FCS}$ of the fuel in a fuel feed system (not shown).

Thereafter, the blending ratio $B_{FCS}$ and at least one of the first and second feedback blending ratios $B_{FB1}$ and $B_{FB2}$ are supplied to a selecting circuit 207. In this selecting circuit 207, one of the control blending ratios B is selected from these plural blending ratios according to a predetermined order of selection, for example, the order of reliability ($B_{FB2} > B_{FB1} > F_{FCS}$).

The control blending ratio B thus obtained (or the fist or second blending ratio compensation coefficient $K_{B1}$ or $K_{B2}$ which includes these blending ratio information) is used for, for example, the ignition timing control for the engine and the computation of the basic driving time $T_B (=A/N(n) \times K_B \times k)$ for the fuel injection valves in the engine fuel feed system per quantity of intake air A/N(n). The symbol k is another compensation coefficient.

Now, an engine control system for the FFV to which the fuel blending ratio detecting method for an embodiment of the present invention is applied will be described by reference to FIG. 3.

Figure 3:
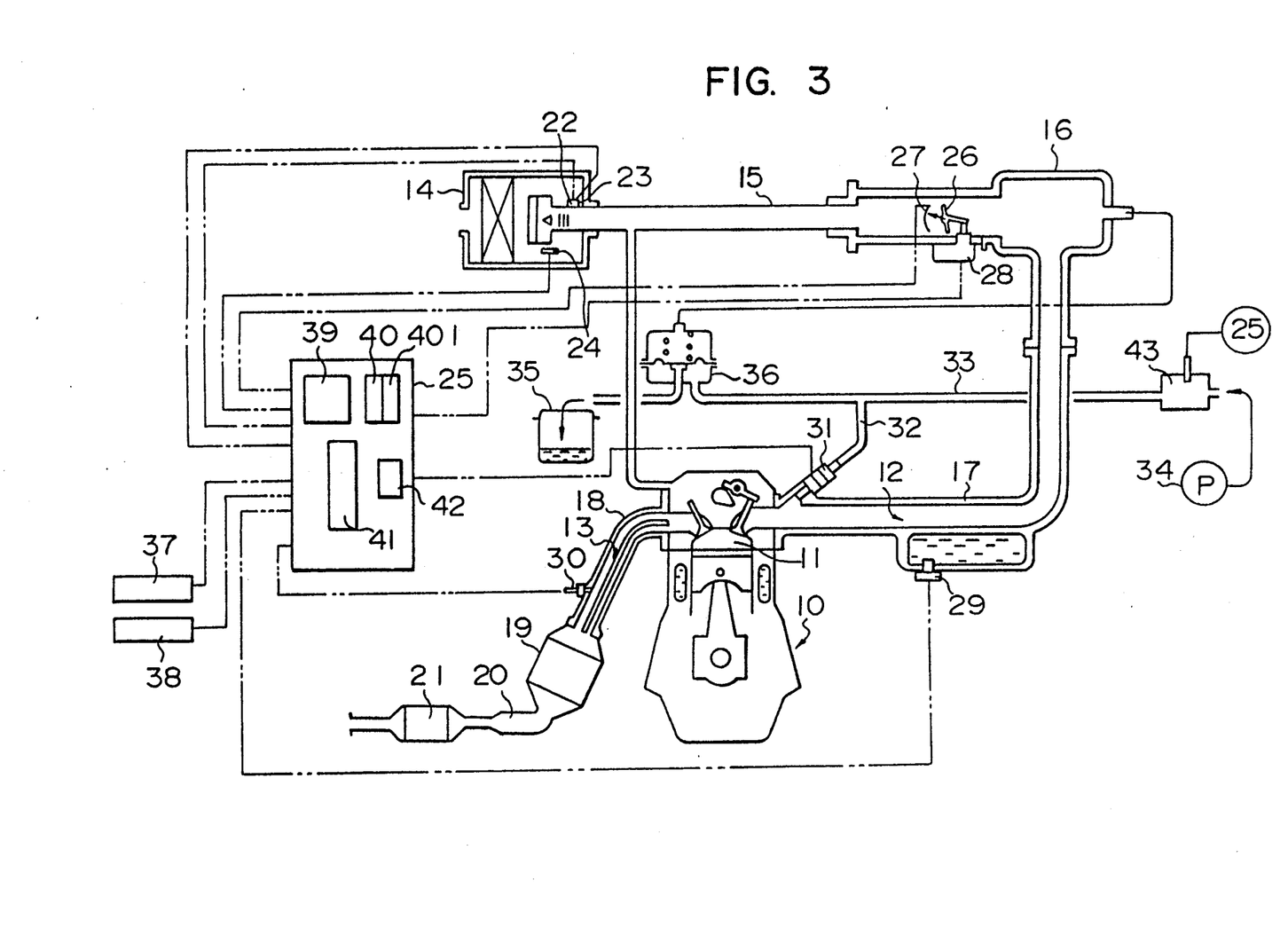
FIG. 3 schematically shows the structure of an engine control system to which the method for an embodiment of the present invention is applied.

Referring to FIG. 3, combustion chambers 11 of an engine 10 communicate with an intake passage 12 and an exhaust passage 13 at a suitable time. The intake passage 12 is formed of an air cleaner 14, a first intake pipe 15, an expansion pipe 16 and a second intake pipe 17. The exhaust passage 13 is formed of a first exhaust pipe 18, a catalyst 19, a second exhaust pipe 20 and a muffler 21.

An air flow sensor 22 generating information regarding the quantity of the flow of air, an atmospheric pressure sensor 23 generating information regarding the atmospheric pressure, and an atmospheric temperature sensor 24 generating information regarding the air temperature are disposed in the air cleaner 14, and they are connected to an engine control unit (referred to hereinafter merely as a controller) 25.

A throttle valve 26 is mounted in the expansion pipe 16, and a throttle position sensor 27 is associated with the throttle valve 26. The idle position of this throttle valve 26 is controlled by the controller 25 through an idle speed control motor (as ISC motor) 28.

A water jacket is associated with part of the second intake pipe 17, and a water temperature sensor 29 is mounted on the water jacket.

Midway of the first exhaust pipe 18, an O₂ sensor 30 is mounted so as to generate information regarding the air/fuel ratio in the exhaust gases from the engine.

Fuel injection valves 31 are mounted at the end of the intake passage 12. Each fuel injection valve 31 is connected to a fuel pipe 33 through a branch pipe 32. This fuel pipe 33 connects between a fuel pump 34 and a fuel tank 35, and, midway of this fuel pipe 33, a blending ratio sensor 43 and a fuel pressure regulator 36 for regulating the fuel pressure are mounted. The blending ratio sensor 43 used herein is of the type well known n the art and such that fuel blending ratio information changing according to the index of refraction is detected by an optical system, and, after photoelectric conversion of the detected change in the quantity of light, the data is supplied to the controller 25. Further, the regulator 36 is constructed so as to regulate the fuel pressure by increasing or decreasing the fuel pressure according to the blood pressure.

In FIG. 3, the numeral 37 designates a crank angle sensor generating information regarding the crank angle, and the numeral 38 designates a top dead center sensor generating information regarding the top dead center of the first cylinder.

The controller 25 includes a control circuit 39, a memory circuit 40, an input/output circuit 41, and a valve driver circuit 42.

The control circuit 39 receives input signals from the individual sensors, and, after processing these input signals according to the control program shown in FIG. 5, generates control signals through the valve driver circuit 42.

The memory circuit 40 stores the control program including a main routine, blending ratio computation, etc. shown in FIGS. 5a to 5f, together with blending ratio maps 4 and 5 similar to those shown in FIG. 1. Further, the memory circuit 40 includes an area for storing the first and second blending ratio compensation coefficients $K_{B1}$, $K_{B2}$, the first and second feedback blending ratios $B_{FB1}$, $B_{FB2}$, the blending ratio $B_{FCS}$, the control blending ratio B, etc. which are used during the control.

The input/output circuit 41 acts to suitably receive the output signals of the individual sensors described above to generate various control signals through driver circuits (not shown) or generate a valve drive signal through the value driver circuit 42 so as to open each of the fuel injection valves 31 at the predetermined timing.

The operation of the controller 25 will now be described together with the control program shown in FIG. 5a to 5f.

When an engine key switch (not shown) is turned on, the controller 25 and the individual sensors start to operate. First, in a step a1 of a main routine shown in FIG. 5a, the controller 25 initializes various settings, measured values, etc. and, in a step a2, executes a blending ratio computation routine.

Figure 5A:
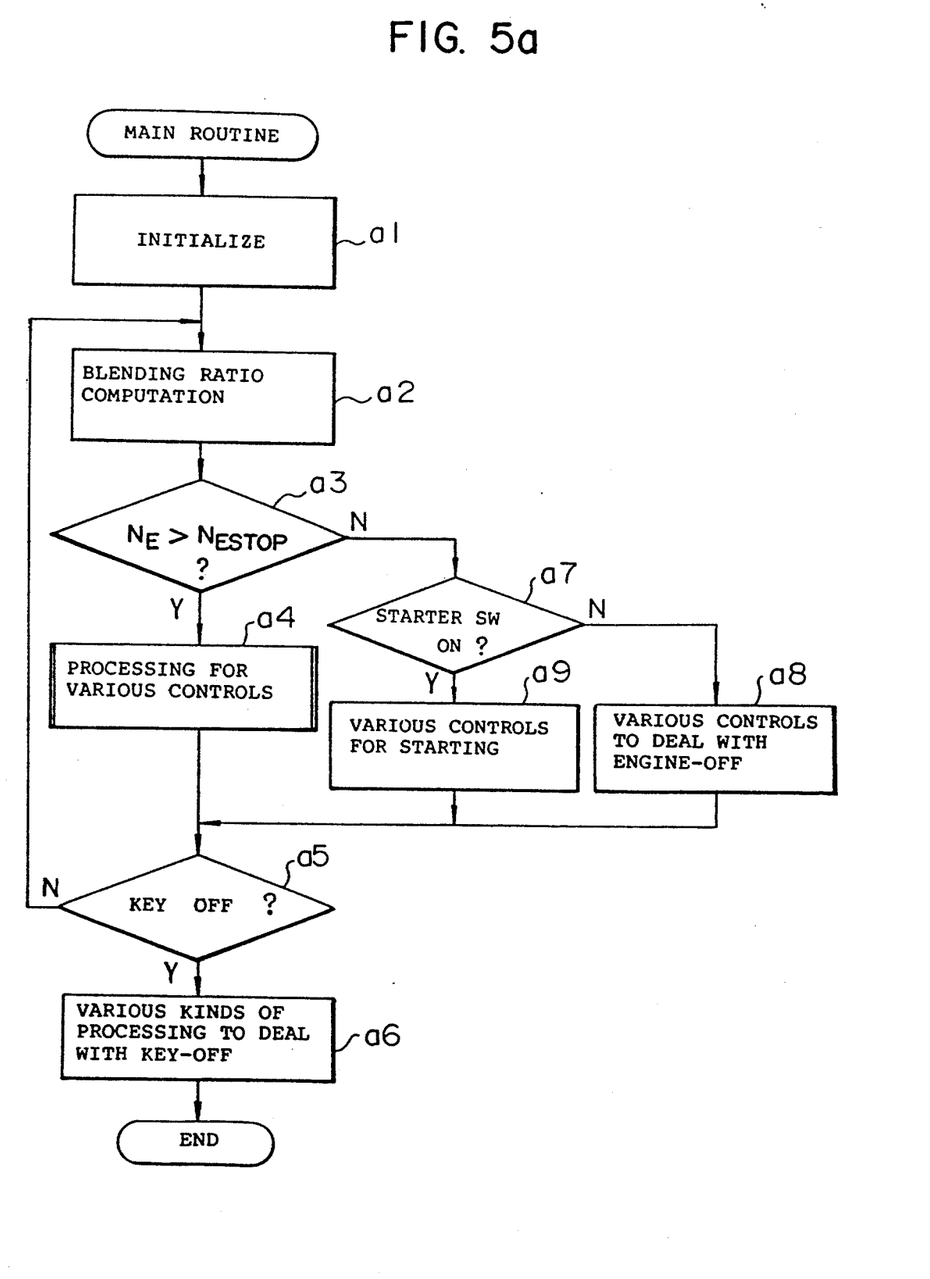
FIGS. 5a to 5f are flow charts of a control program executed by the system shown in FIG. 3 for the engine control purpose.
Figure 5B:
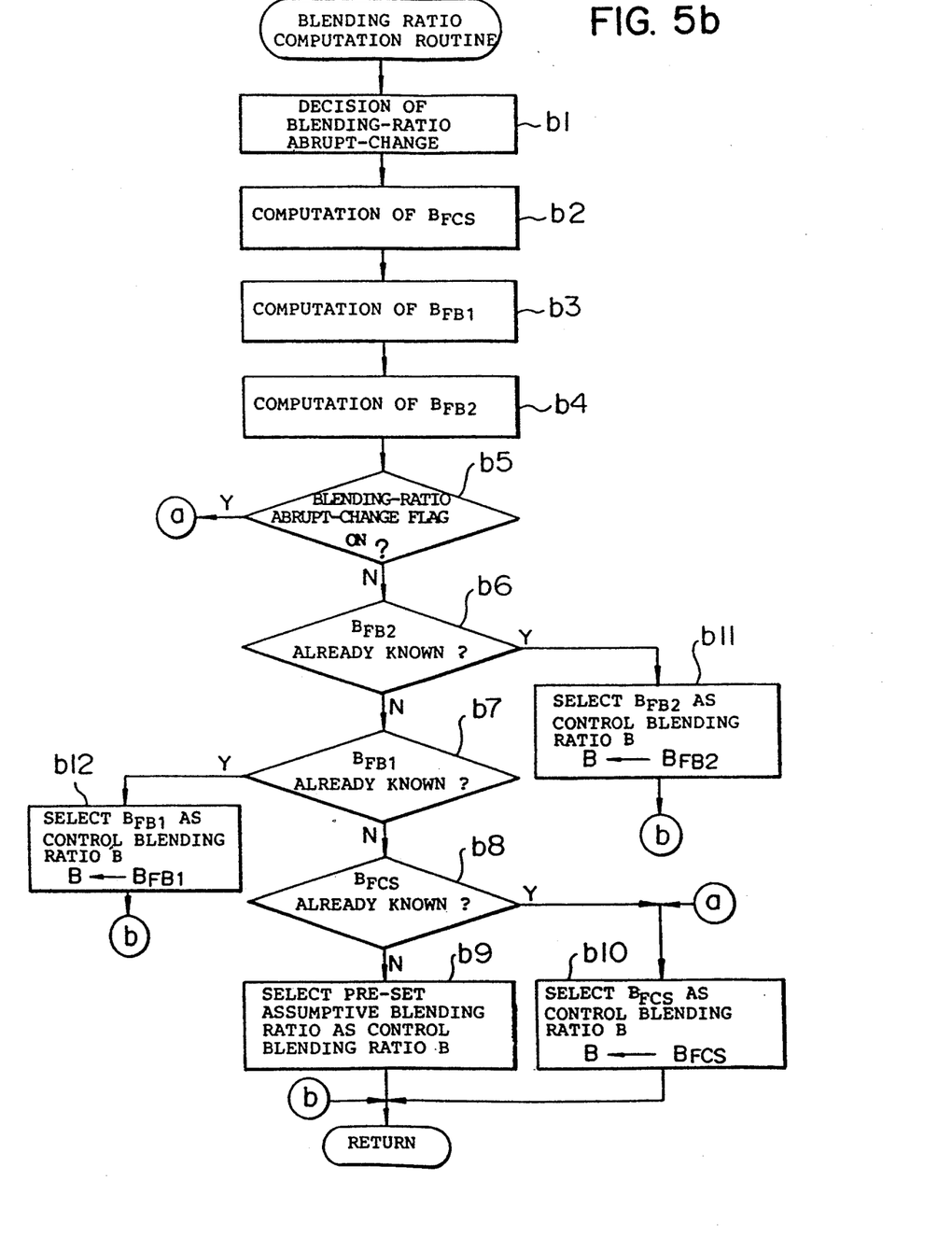

In this blending ratio computation routine shown in FIG. 5b, firstly, in a step b1, a blending-ratio abrupt-change decision routine is executed so as to decide whether or not an abrupt change has occurred on the blending ratio.

Figure 5C:
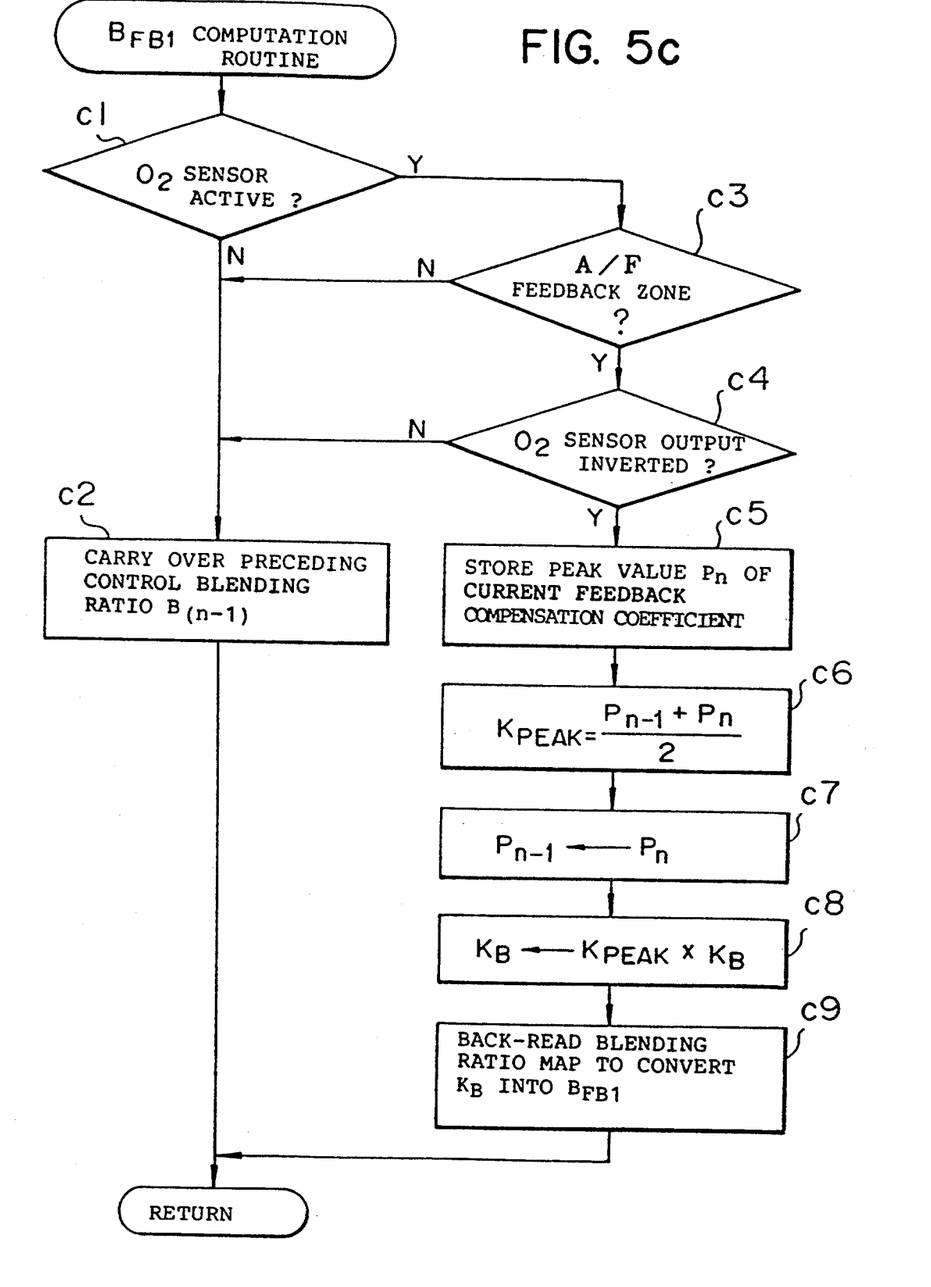
Figure 5D:
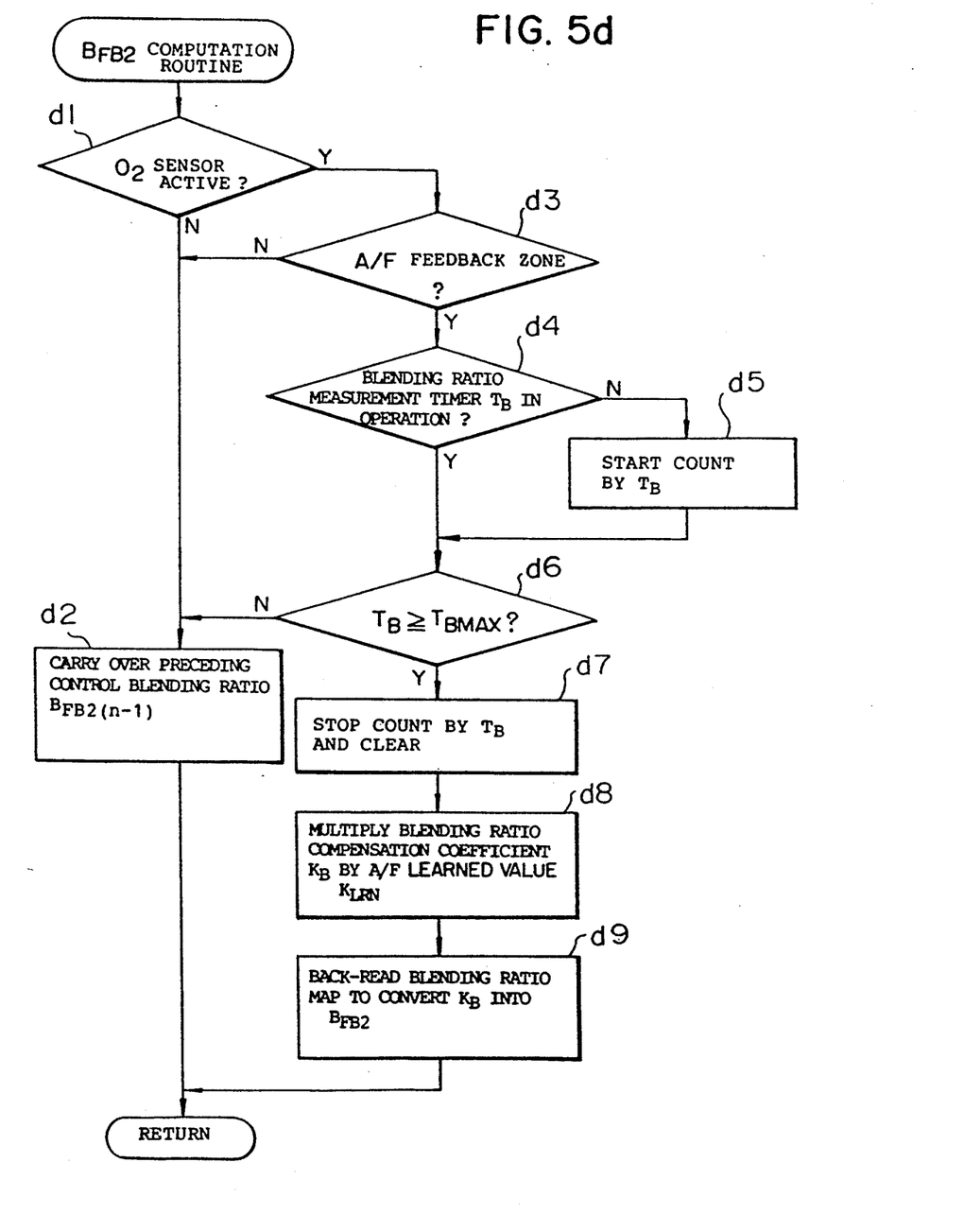
Figure 5E:
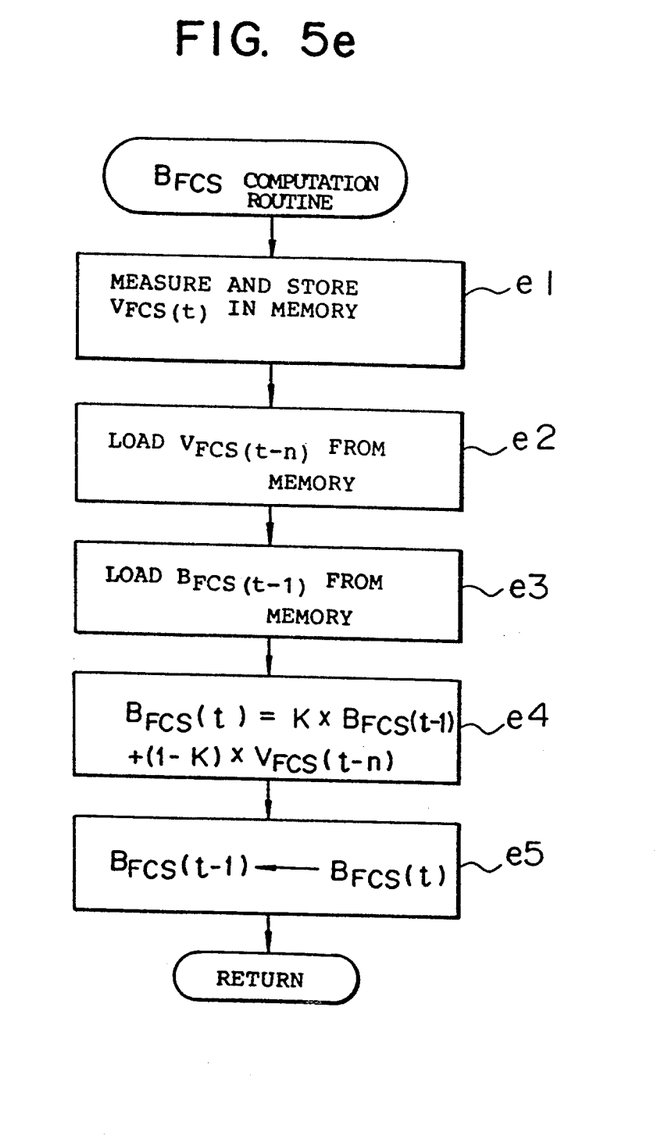
Figure 5F:
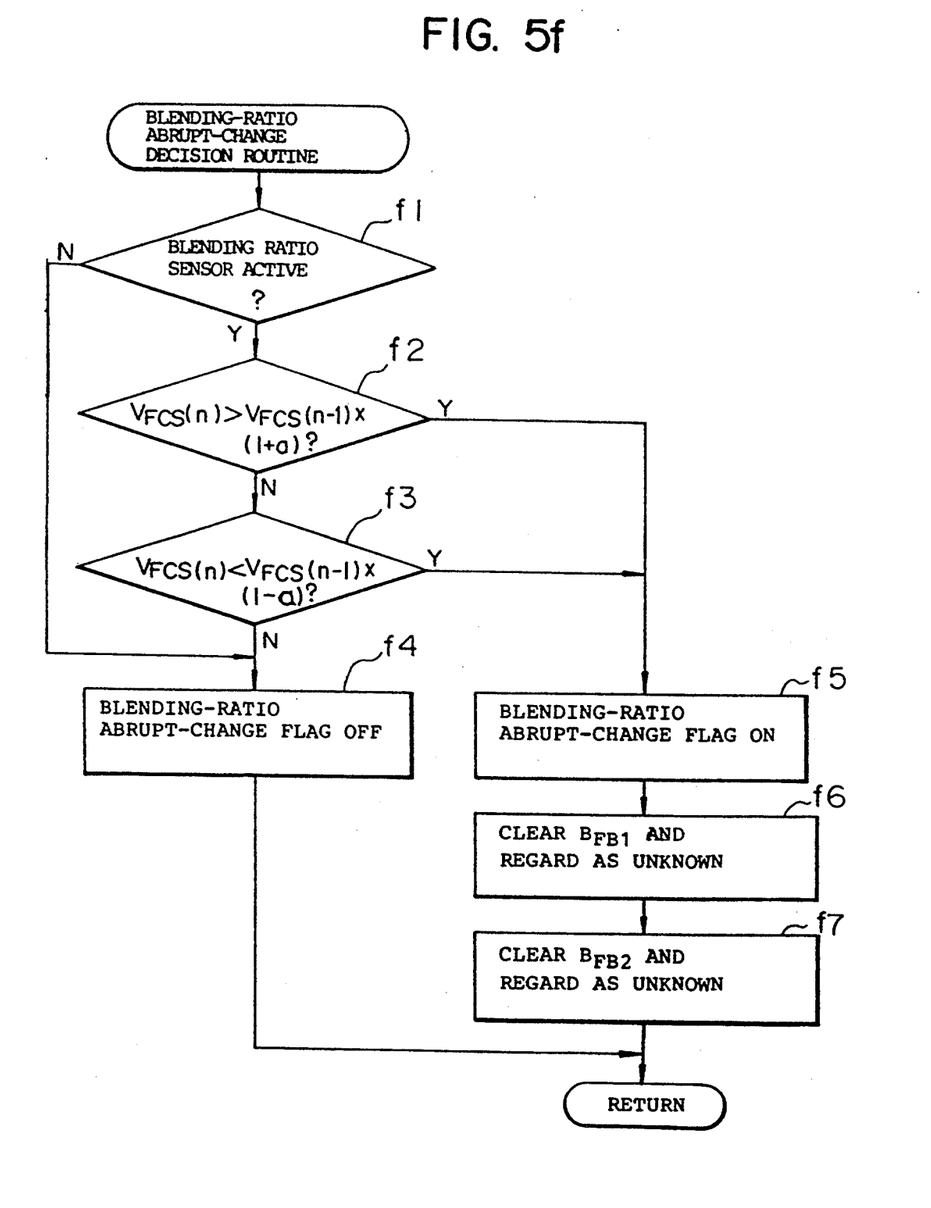

In this blending-ratio abrupt-change decision routine shown in FIG. 5f, firstly, in a step F1, whether the blending ratio sensor 43 is active or not is decided on the basis of, for example, the temperature of the fuel. When the blending ratio sensor 43 is decided to be inactive, the step f1 is followed by a step f4, and the program returns after turning off a blending-ratio abrupt-change flag. On the other hand, when the blending ratio sensor 43 is decided to be active, the step f1 is followed by a step f2.

In the step f2, the current output $V_{FCS}(n)$ of the blending ratio sensor 43 is compared with the value obtained by multiplying the preceding output $V_{FCS}(n-1)$ by an increment $(1+a)$. When the current value shows an increase over the preceding value, the step f2 is followed by a step f5, and when the former does not show any increase, the step f2 is followed by a step f3. In this step f3, the current output $V_{FCS}(n)$ is compared with the value obtained by multiplying the preceding output $V_{FCS}(n-1)$ by a decrement $(1-a)$. When the current value shows a decrease, the step f3 is followed by the step f5, and when the former does not show any decrease, the step f3 is followed by the step f4.

Deciding that an abrupt change has occurred on the blending ratio, the blending-ratio abrupt-change flag is turned on in the step f5. Then, in a step f6, the first feedback blending ratio $B_{FB1}$ is cleared, and a flag indicating that this ratio is unknown is registered. Similarly, in a step f7, the second feedback blending ratio $B_{FB2}$ is cleared, and a flag indicating that this ratio is unknown is registered. Then, the program returns.

When the program returns to a step b2 of the blending ratio computation routine shown in FIG. 5b, the blending ratio $B_{FCS}$ is computed on the basis of the output of the blending ratio sensor 43.

In this routine shown in FIG. 5e, firstly, in a step e1, the output $V_{FCS}(t)$ of the blending ratio sensor 43 is measured and stored in the memory. Then, in a step e2, the output $V_{FCS}(t-n)$ of the blending ratio sensor 43 measured n times before is loaded from the memory. In a step e3, the blending ratio $B_{FCS}(t-1)$ computed at the preceding time is loaded from the memory. Then, in a step e4, the current blending ratio $B_{FCS}(t)$ is computed according to the following equation:

$$B_{FCS}(t) = K \times B_{FCS}(t-1) + (1-K) \times V_{FCS}(t-n)$$

In the equation, K is a filter constant, and n is a delay of the fuel feed. Then, in a step e5, the blending ratio $B_{FCS}(t)$ is updated, and the program returns.

When the program returns to a step b3 of the blending ratio computation routine shown in FIG. 5b, a $B_{FB1}$ computation routine is executed in which the first feedback blending ratio $B_{FB1}$ is computed on the basis of the output of the O₂ sensor 30.

In this routine shown in FIG. 5c, firstly, whether or not the O₂ sensor 30 is active is decided in a step c1 according to the following conditions: 1. The O₂ sensor is decided to be inactive when the engine is stopped. 2. The sensor is decided to be active when the sensor output crosses a predetermined level (for example, 0.6 V) when 15 seconds has elapsed after the engine is stalled and started. 3. The sensor is decided to be inactive when the state where the sensor output does not cross a predetermined level (for example, 0.6 V) continues over a predetermined period (for example, 20 seconds) during the feedback, control.

When the O₂ sensor 30 is not decided to be active, the step c1 is followed by a step c2 in which the preceding blending ratio B(n−1) is used, and then the program returns.

On the other hand, when the O₂ sensor 30 is decided to be active, the step c1 is followed by a step c3 which decides whether or not the engine is in an air/fuel ratio feedback zone. The conditions for deciding that the engine is in the air/fuel ratio feedback zone are, for example, as follows: 1. The temperature of water is higher than 75° C. 2. The temperature of intake air is higher than 50° C. 3. The atmospheric pressure ranges from 580 to 800 mmHg. 4. The engine is neither in its accelerating range nor in its decelerating range. 5. The engine is not operating in a very low speed range. 6. There is no change in the operating zone of the engine.

When the engine is decided not to be in the air/fuel ratio feedback zone, the step c3 is followed by the step c2. On the other hand, when the engine is decided to be in the air/fuel ratio feedback zone, the step c3 is followed by a step c4 which decides whether or not the magnitude relation between the output of the O₂ sensor 30 and the decision voltage $V_{Ref}$ is inverted. The preceding sensor output is expressed as $V_{n-1}$, the current sensor output is expressed as $V_N$, and the rich/lean decision voltage is expressed as $V_{ref}$, and these values are successively updated and stored in the predetermined area. Then, the signs of $(V_{n-1}-V_{ref})$ and $(V_N-V_{Ref})$ are compared, and, when the signs are different, the magnitude relation is decided to be inverted now.

Figure 4A:
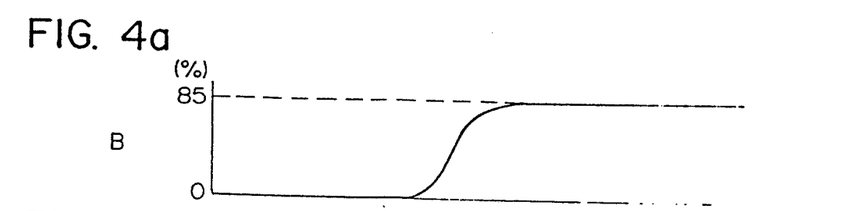
FIGS. 4a to 4j are waveform diagrams showing how the characteristic values in the engine control system shown in FIG. 3 change with time.
Figure 4B:
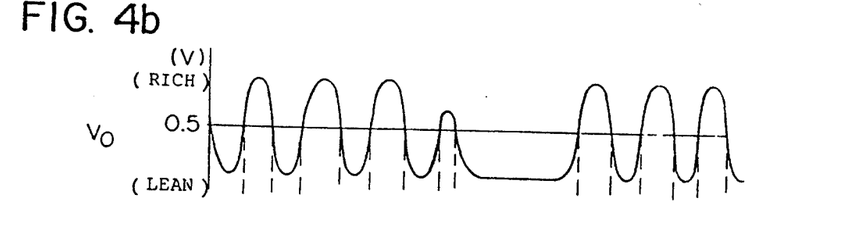
Figure 4C:
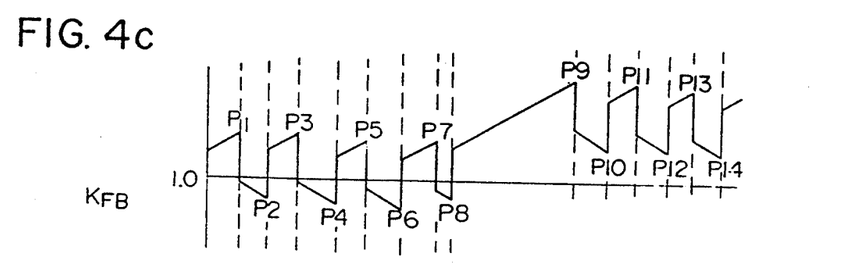

When the output of the O₂ sensor 30 is decided not to be inverted in the step c4, the step c4 is followed by the step c2. On the other hand, when the sensor output is inverted, that is, when the sensor output crosses the decision voltage $V_S$ (=0.5 V) shown in FIG. 4b, the step c4 is followed by a step c5. In this step c5, the peak values $P_n$ of the current feedback compensation coefficient $K_{FB}$ (for example, the maximum and minimum values $P_1$, $P_2$, $P_3$... shown in FIG. 4c) are stored in the predetermined area. Then, in a step c6, the mean value of the preceding peak value $P_{n-1}$ and the current peak value $P_n$ is computed as the peak means value $K_{PEAK}$ $[=(P_{a-1}+P_n)/2]$. Then, in a step c7, the peak value $P_n$ is stored in the memory as the preceding peak value $P_{n-1}$.

It is supposed now that the blending ratio B of the fuel is changed from 100% of gasoline to 85% of methanol. (Refer to FIG. 4a.)

Figure 4D:
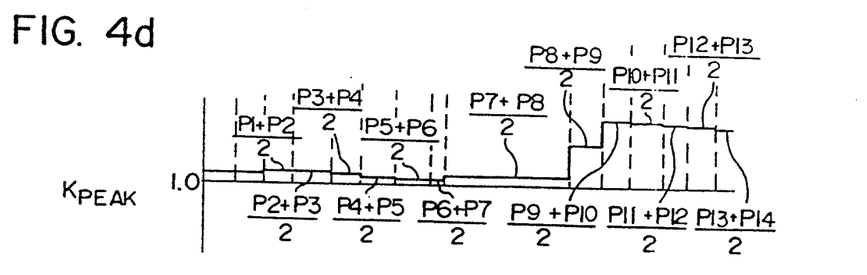
Figure 4E:
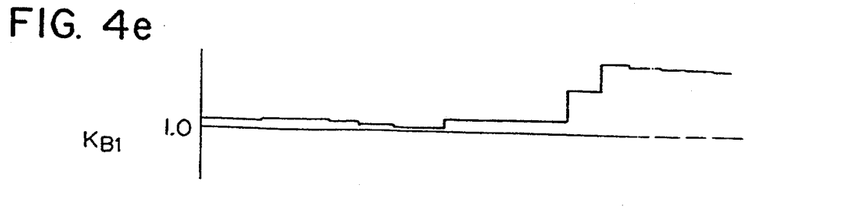
Figure 4F:
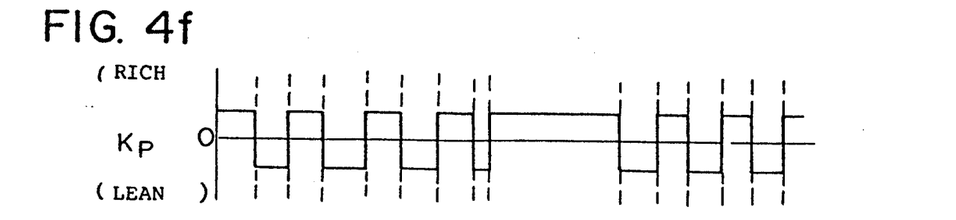
Figure 4G:
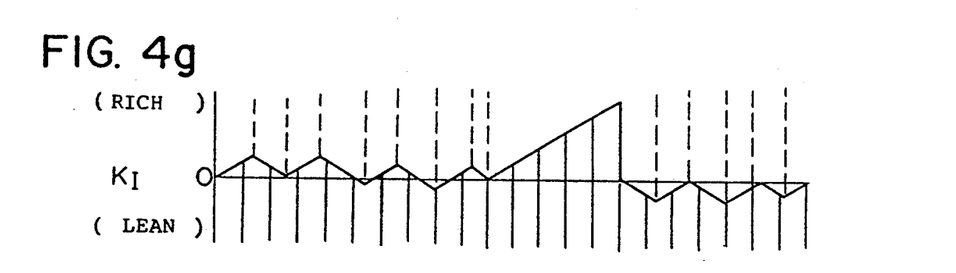

In this case, because the stoichiometric air/fuel ratio of the methanol is lower than that of the gasoline (shortage of fuel), the sensor output $V_0$ continues to fluctuate on the lean side. (Refer to FIG. 4b.) Then, the feedback compensation coefficient $K_{FB}$ (=1.0+$K_1$+$K_P$) obtained by proportionating and integrating the proportional gain and the integral gain continues to increase or decrease on the rich side depending on the magnitude relation between the sensor output $V_0$ and the decision voltage $V_S$. (Refer to FIGS. 4c, 4f and 4g.)

Then, in a step c8, the first blending ratio compensation coefficient $K_{B1}$ is read out from the predetermined area, and this value is multiplied by the peak mean value $K_{PEAK}$ so as to update $K_{B1}$ ($K_{B1}\rightarrow K_{B1}\times K_{PEAK}$). (Refer to FIGS. 4d and 4e.)

The, in a step c9, the controller 25 back-reads the first blending ratio map 4 (shown in FIG. 1) in a direction as shown by the arrow in FIG. 1, and the first feedback blending ratio $B_{FB1}$ is computed on the basis of the updated first blending ratio compensation coefficient $K_{B1}$. The program then returns.

After the above change in the fuel blending ratio, the percentage of the gasoline is 15%, and that of the methanol is 85%. When the fuel having this gasoline and methanol blending ratio is used, the actual sensor output $V_N$ swings vertically around about 0.5 V, and thus the mixed fuel is regarded to be supplied in a quantity enough to substantially maintain the stoichiometric air/fuel ratio.

When the program returns to a step b4 of the blending ratio computation routine shown in FIG. 5b, a $B_{FB2}$ computation routine is executed in which the second feedback blending ratio $B_{FB2}$ is computed on the basis of the output of the O₂ sensor 30.

First, in a step d1 shown in FIG. 5d, whether or not the O₂ sensor 30 is active is decided according to the aforementioned conditions for decision. When the O₂ sensor 30 is not decided to be active, the step d1 is followed by a step d2 in which the preceding second feedback blending ratio $B_{FB2}(n-1)$ is used, and then the program returns.

When, on the other hand, the O₂ sensor 30 is decided to be active, the step d1 is followed by a step d3 which decides whether the engine is in the air/fuel ratio feedback zone or not according to the aforementioned conditions for decision.

When the engine is decided not to be in the air/fuel feedback zone, the step d3 is followed by the step d2, while when the engine is decided to be in that zone, the step d3 is followed by a step d4.

In the step d4, whether a blending ratio measurement timer $T_B$ is operating or not is decided. When the blending ratio measurement timer $T_B$ is decided not to be operating, the timer is started in a step d5. In a step d6, counting of a time $T_{BMAX}$ by the blending ratio measurement timer $T_B$ is detected. Before the above time is counted, the step d6 is followed by the step d2, while after the above time is counted, the step d6 is followed by a step d7.

In the step d7, the blending ratio measurement timer $T_B$ is stopped and cleared. Then, in a step d8, the second blending ratio compensation coefficient $K_{B2}$ is read out from the predetermined area, and the feedback learned value $K_{LNR}$ learned during the blending ratio measurement period $T_B$ is multiplied by the second blending ratio compensation coefficient $K_{B2}$ to update the value of $K_{B2}$ ($K_{B2}\rightarrow K_{B2}\times K_{LRN}$).

It is supposed now that the blending ratio B of the fuel is changed from 100% of gasoline to 85% of methanol. (Refer to FIG. 4a.)

In this case, because the stoichiometric air/fuel ratio of the methanol is lower than that of the gasoline (shortage of fuel), the sensor output $V_0$ continues to fluctuate on the lean side. (Rewfer to FIG. 4b.) Then, due to the magnitude relation between the sensor output $V_0$ and the decision voltage $V_S$, the integral compensating term $K_1$ of the feedback compensation coefficient obtained by integrating the integral gain continues to increase or decrease on the rich side. (Refer to FIG. 4g.)

Figure 4H:
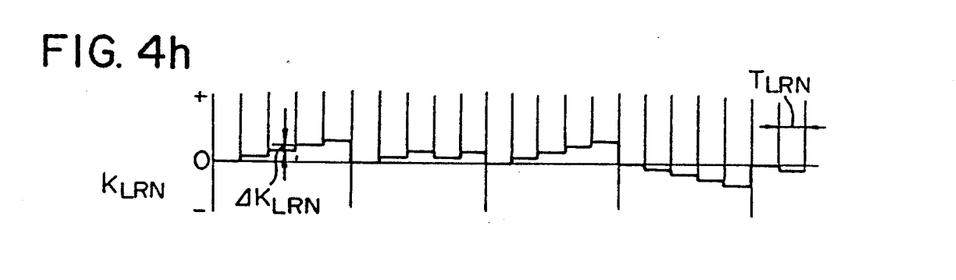
Figure 4I:
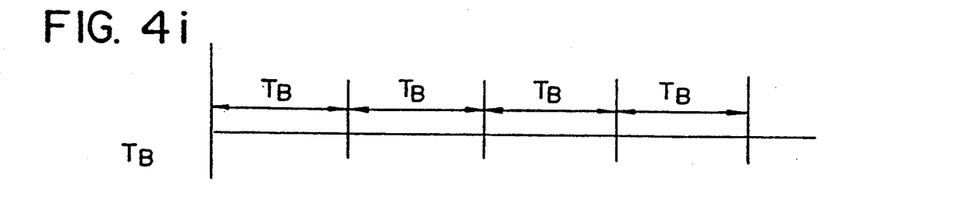
Figure 4J:
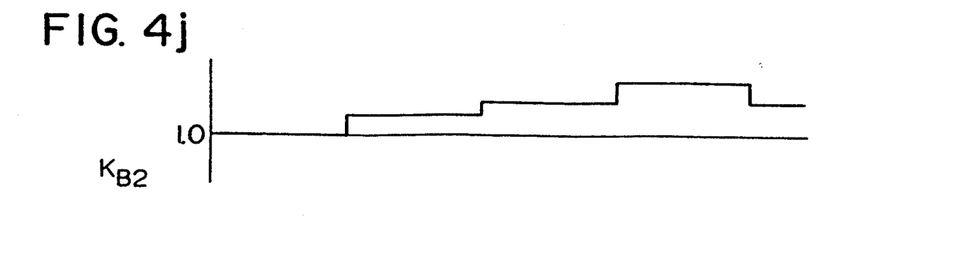

The feedback learned value $K_{LRN}$ starts from zero each time the predetermined blending ratio measurement period $T_B$ starts. Depending on whether the integral compensating term $K_1$ of the air/fuel ratio feedback compensation coefficient $K_{FB}$ is decided to be positive or negative in each predetermined learning cycle $T_{LRN}$ (of, for example, 25 milliseconds), the predetermined value $\Delta K_{LRN}$ is added to or subtracted from the feedback learned value $K_{IRN}$ obtained immediately before. (Refer to FIGS. 4h and 4i.) Further, the feedback learned value $K_{LRN}$ updated in each predetermined learning cycle $T_{LRN}$ is added to or subtracted from the preceding second blending ratio compensation coefficient $K_{B2}$ at the time of counting $T_{BMAX}$ of the blending ratio measurement period $T_B$. Thus, the second blending ratio compensation coefficient $K_{B2}$ is updated at the end of each predetermined blending ratio measurement period $T_B$. (Refer to FIG. 4j.)

Then, in a step d9, the controller 25 back-reads the second blending ratio map 5 (shown in FIG. 1) in a direction as shown by the arrow in FIG. 1, and the second feedback blending ratio $B_{FB2}$ is computed on the basis of the updated second blending ratio compensation coefficient $K_{B2}$. The program then returns.

The program returns to a step b5 of the blending ratio computation routine shown in FIG. 5b. In this step, when the blending-ratio abrupt-change flag is on, the step b5 is followed by a step b10, while when the flag is off, the step b5 is followed by a step b6.

In the step b10, the output $B_{FCS}$ of the blending ratio sensor 43 is selected as the control blending ratio B, and the program returns.

On the other hand, when there is no abrupt change in the blending ratio and the step b5 is followed by the step b6, whether or not the second feedback blending ratio $B_{FB2}$ is already known is checked. When this ratio is already known, the step b6 is followed by a step b11 on which the second feedback blending ratio $B_{FB2}$ is selected as the control blending ratio B, and the program returns.

On the other hand, when the step b6 is followed by a step b7, whether or not the first feedback blending ratio is already known is decided. When this ratio is already known, the step b7 is followed by a step b12 in which the first feedback blending ratio $B_{FB1}$ is selected as the control blending ratio B, and the program returns.

On the other hand, when the step b7 is followed by a step b8, decision is made as to whether or not the blending ratio $B_{FCS}$ detected by the blending ratio sensor 43 is already known. When this ratio is already known, the step b8 is followed by the step b10 in which the blending ratio $B_{FCS}$ is selected as the control blending ratio B, and the program returns. When none of these blending ratios is known, the step c8 is followed by the step b9. In this step c9, a pre-set assumptive blending ratio (which is suitably set according to the vehicle type, vehicle driving mode, vehicle driving area, etc.) is selected as the control blending ratio B, and the program returns.

After the blending ratio computation routine is executed, the program returns to a step a3 of the main routine shown in FIG. 5a. In the step a3, the engine rotation speed $N_E$ is detected, and decision is made as to whether or not the detected engine rotation speed is higher than an engine operation decision speed $N_{ESTOP}$.

When a step a4 is reached during the rotation of the engine, the control blending ratios $B_{FB1}$ and $B_{FB2}$ are suitably read out so as to carry out various kinds or processing including processing for controlling the quantity of fuel injection and processing for controlling the ignition timing.

Among the various kinds of processing carried out in the step a4, how to compute the fuel injection valve driving time $T_{inj}$ will be described as an example. First, the basic driving time $T_B$ [$=A/N(n) \times K_B \times k$] per unit intake air quantity is computed. This blending ratio compensation coefficient $K_B$ is used so that the basic driving time $T_B$ (the basic fuel quantity) per predetermined intake air quantity $A/N(n)$ can be regulated to the value corresponding to the blending ratio of the supplied fuel. Then, the fuel injection valve driving time $T_{imj}$ is computed using the basic driving time $T_B$ and compensated values of the feedback compensation coefficient $K_{FB}$, atmospheric air temperature compensation coefficient Kt, atmospheric pressure compensation coefficient Kwt, and acceleration compensation coefficient Kwt, and acceleration compensation coefficient Kac. ($T_{inj} = T_B \times K_{FB} \times Kt \times Kb \times Kwt \times Kac$) The feedback compensation coefficient $K_{FB}$ in the above expression is shown as the proportional and integral value of the air/fuel ratio, that is, the sum of the proportional compensating term $K_P$ and the integral compensating term $K_1$.

When a step a5 is reached after the various kinds of processing are carried out, decision is made as to whether or not the key is off. When the key is not off, the step 15 is followed by the step a2, while when the key is off, the step a5 is followed by a step a6 in which various kinds of processing at the key-off such as, for example, processing for storing data in a non-volatile memory are carried out to complete the main routine.

When the engine is stopped, the step a3 is followed by a step a7 in which whether or not the starter switch is on is checked. When the starter switch is off, the step a7 is followed by a step a8. In this step a8, predetermined steps of processing corresponding to the engine stoppage are carried out. On the other hand, when the starter switch is on, the step a7 is followed by a step a9. In this step a9, various kinds of processing necessary for starting the vehicle are carried out, and the step a9 is followed by the step a5.

When the engine is stopped, the control blending ratio used at that time is stored as a memory blending ratio $B_{MEM}$ in a backup memory 401 (FIG. 3). Upon re-starting of the engine thereafter, this memory blending ratio $B_{MEM}$ is read out and generated as the control blending ratio B for a predetermined period only. After the predetermined period described above elapses, the blending ratio $B_{FCS}$ detected by the blending ratio sensor 43 is generated as the control blending ratio B.

It will be seen in the foregoing description that three blending ratios, that is, the first and second feedback blending ratios $B_{FB1}$ and $B_{FB2}$ and the blending ratio $B_{FCS}$ are selected, and the priority order of selection is in the order of the second feedback blending ratio $B_{FB2}$, the first feed blending ratio $B_{FB1}$ and the blending ratio $B_{FCS}$. However, only one of the first and second feedback blending ratios $B_{FB1}$ and $B_{FB2}$ is first selected, and the preferred one of that value and the blending ratio $B_{FCS}$ may be selected as the control blending ratio.

It will be understood from the foregoing description that, in the method of the present invention, a first feedback blending ratio $B_{FB1}$ is obtained by computing a peak mean value of feedback compensation coefficients computed on the basis of an air/fuel ratio indicative output of an $O_2$ sensor, updating a blending ratio compensation coefficient on the basis of the peak mean value, and computing on the basis of the updated blending ratio compensation coefficient, or obtaining a second feedback blending ratio $B_{FB2}$ by obtaining a feedback learned value on the basis of the air/fuel ratio indicative output of the sensor, updating a blending ratio compensation coefficient and computing on the basis of the updated blending ratio compensation coefficient, and further detecting a blending ratio $B_{FCS}$ from a blending ratio sensor. Therefore, one of these blending ratios can be suitably selected to be generated as the control blending ratio, so that a blending ratio very close to the true blending ratio can be always detected.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. A fuel blending ratio detecting device for an internal combustion engine comprising:

a blending ratio sensor disposed in a fuel path for feeding fuel to the internal combustion engine to detect a first blending ratio of methanol;

an $O_2$ sensor for generating information of an air/fuel ratio in exhaust gases from the internal combustion engine, said $O_2$ sensor output being increased or decreased with time relative to a rich/lean decision voltage;

fuel control means for computing an air/fuel ratio feedback compensation coefficient from an integral control of the output of said $O_2$ sensor to regulate the quantity of supplied fuel so that an air/furl ratio of the fuel mixture supplied to the internal combustion engine corresponds to a predetermined target value;

a first computing means for computing a feedback learned value at intervals of a first predetermined period as a result of said integral control on the basis of the factor of the feedback compensation coefficient and multiplying the current blending ratio compensation coefficient by said feedback learned value to compute the next blending ratio compensation coefficient so as to compute a second blending ratio on the basis of said next blending ratio compensation coefficient;

second computing means for computing a peak mean value of the current and preceding peak values of said feedback compensation coefficient each time peak values appear and multiplying the current blending ratio compensation coefficient by said peak mean value to compute the next blending ratio compensation coefficient so as to compute a third blending ratio on the basis of said next blending ratio compensation coefficient; and selecting means for selecting one of said first, second and third blending ratios according to the operating conditions of the internal combustion engine.

2. A device according to claim 1, wherein said third blending ratio is first used after said $O_2$ sensor becomes active.

3. A device according to claim 1, wherein said second blending ratio is used after said second blending ratio is detected.

4. A device according to claim 1, wherein said first blending ratio is used when said second blending ratio or said third blending ratio changes over more than a predetermined value within a predetermined period.

5. A device according to claim 1, further comprising a memory for storing the blending ratio used when the internal combustion engine is stopped and the blending ratio stored in said memory is used for a predetermined period when the internal combustion engine started later.

6. A device according to claim 5, wherein said first blending ratio is used after lapse of said predetermined period.

* * * * *